(12) United States Patent
Wood (10) Patent No.: US 7,191,781 B2
(45) Date of Patent: Mar. 20, 2007

(54) NASAL VENTILATION INTERFACE AND SYSTEM

(75) Inventor: Thomas J. Wood, Blackshear, GA (US)

(73) Assignee: Innomed Technologies, Inc., Coconut Creek, FL (US)

( * ) Notice: Subject to any disclaimer, the term of this patent is extended or adjusted under 35 U.S.C. 154(b) by 0 days.

(21) Appl. No.: 11/007,218

(22) Filed: Dec. 9, 2004

(65) Prior Publication Data

US 2005/0133039 A1    Jun. 23, 2005

Related U.S. Application Data (63) Continuation-in-part of application No. 10/910,616, filed on Aug. 4, 2004, which is a continuation-in-part of application No. 10/830,034, filed on Apr. 23, 2004.

(60) Provisional application No. 60/501,028, filed on Sep. 9, 2003, provisional application No. 60/492,282, filed on Aug. 5, 2003.

(51) Int. Cl.
*A61M 16/00* (2006.01)
*A61M 15/08* (2006.01)
(52) U.S. Cl. .............................. 128/206.11; 128/207.18
(58) Field of Classification Search ........... 128/201.28, 128/203.29, 204.12, 204.26, 205.23, 205.24, 128/205.25, 205.27, 206.11, 206.12, 206.15, 128/206.18, 206.21, 207.11, 207.13, 207.18; 600/529, 532, 538; 137/908
See application file for complete search history.

(56) References Cited

U.S. PATENT DOCUMENTS

| | | | | |
|---|---|---|---|---|
| 1,125,542 | A | | 1/1915 | Humphries |
| 3,097,642 | A | * | 7/1963 | Russell ................. 128/205.17 |
| 3,670,726 | A | | 6/1972 | Mahon et al. |
| 3,674,910 | A | * | 7/1972 | McKenzie ................... 84/377 |
| 3,739,774 | A | | 6/1973 | Gregory |
| 3,861,385 | A | | 1/1975 | Carden |
| 3,902,486 | A | | 9/1975 | Guichard |
| 3,905,381 | A | | 9/1975 | Hewson et al. |
| 3,913,607 | A | * | 10/1975 | Price ............................ 137/271 |
| 4,138,105 | A | * | 2/1979 | Hunger et al. ................ 482/13 |
| 4,156,426 | A | | 5/1979 | Gold |
| 4,221,381 | A | * | 9/1980 | Ericson ........................ 482/13 |
| 4,267,845 | A | | 5/1981 | Robertson, Jr. et al. |
| 4,273,124 | A | | 6/1981 | Zimmerman |

(Continued)

FOREIGN PATENT DOCUMENTS

DE         146688       2/1981

(Continued)

OTHER PUBLICATIONS

SNAPP Nasal Interface, Tiara Medical Systems, Inc. http://www.tiaramed.com/asp_shop/shopdisplayproducts.asp?id=109 &cat=SNAPP%2A+NASAL+Interface, viewed May 17, 2005.

*Primary Examiner*—Teena Mitchell
(74) *Attorney, Agent, or Firm*—Maier & Maier, PLLC (57) ABSTRACT

A ventilation interface and system is described which can be adapted to be connected to a source of ventilation. The ventilation interface and system may include variable exhaust ports. The ventilation interface system may optionally include feed tubes, y-connector, tube holder, and headgear.

4 Claims, 9 Drawing Sheets

U.S. PATENT DOCUMENTS

| | | | |
|---|---|---|---|
| 4,312,359 A | 1/1982 | Olson | |
| 4,367,735 A | 1/1983 | Dali | |
| 4,367,816 A | 1/1983 | Wilkes | |
| 4,406,283 A | 9/1983 | Bir | |
| 4,422,456 A | 12/1983 | Tiep | |
| 4,493,614 A | 1/1985 | Chu et al. | |
| 4,549,542 A | 10/1985 | Chien | |
| 4,587,967 A | 5/1986 | Chu et al. | |
| 4,601,465 A | 7/1986 | Roy | |
| 4,617,637 A | 10/1986 | Chu et al. | |
| 4,660,555 A | 4/1987 | Payton | |
| 4,699,139 A | 10/1987 | Marshall et al. | |
| 4,706,664 A | 11/1987 | Snook et al. | |
| 4,753,233 A | 6/1988 | Grimes | |
| 4,774,946 A | 10/1988 | Ackerman et al. | |
| 4,899,740 A | 2/1990 | Napolitano | |
| 4,915,105 A | 4/1990 | Lee | |
| 4,996,983 A | 3/1991 | AmRhein | |
| 5,000,173 A | 3/1991 | Zalkin et al. | |
| 5,022,900 A | 6/1991 | Bar-Yona et al. | |
| 5,025,805 A | 6/1991 | Nutter | |
| 5,038,772 A | 8/1991 | Kolbe et al. | |
| 5,046,491 A | 9/1991 | Derrick | |
| 5,074,297 A | 12/1991 | Venegas | |
| 5,113,857 A | 5/1992 | Dickerman et al. | |
| 5,121,745 A | 6/1992 | Israel | |
| 5,127,397 A | 7/1992 | Kohnke | |
| 5,137,017 A | 8/1992 | Salter | |
| D333,015 S | 2/1993 | Farmer et al. | |
| 5,188,101 A | 2/1993 | Tumolo | |
| 5,265,592 A | 11/1993 | Beaussant | |
| 5,265,595 A | 11/1993 | Rudolph | |
| 5,269,296 A | 12/1993 | Landis | |
| 5,271,391 A | 12/1993 | Graves | |
| 5,280,780 A * | 1/1994 | Abel | 128/203.14 |
| 5,299,599 A | 4/1994 | Farmer et al. | |
| 5,335,656 A | 8/1994 | Bowe et al. | |
| 5,355,893 A | 10/1994 | Mick et al. | |
| 5,372,130 A | 12/1994 | Stern et al. | |
| 5,375,593 A | 12/1994 | Press | |
| 5,385,141 A | 1/1995 | Granatiero | |
| 5,394,568 A | 3/1995 | Brostrom et al. | |
| 5,396,885 A | 3/1995 | Nelson | |
| 5,398,676 A | 3/1995 | Press et al. | |
| 5,400,776 A | 3/1995 | Bartholomew | |
| 5,425,359 A | 6/1995 | Liou | |
| 5,437,267 A | 8/1995 | Weinstein et al. | |
| 5,509,409 A | 4/1996 | Weatherholt | |
| 5,526,806 A | 6/1996 | Sansoni | |
| 5,533,506 A | 7/1996 | Wood | |
| 5,557,049 A * | 9/1996 | Ratner | 73/715 |
| 5,682,881 A | 11/1997 | Winthrop et al. | |
| 5,740,799 A | 4/1998 | Nielsen | |
| 5,794,619 A | 8/1998 | Edelman et al. | |
| 5,906,203 A | 5/1999 | Klockseth et al. | |
| 5,954,049 A | 9/1999 | Foley et al. | |
| 6,561,188 B1 | 5/2003 | Ellis | |
| 6,561,193 B1 | 5/2003 | Noble | |
| 6,571,798 B1 | 6/2003 | Thornton | |
| 6,595,215 B2 | 7/2003 | Wood | |
| 6,637,434 B2 | 10/2003 | Noble | |
| 6,647,983 B2 * | 11/2003 | Smith et al. | 128/205.24 |
| 6,655,385 B1 | 12/2003 | Curti et al. | |
| 6,679,265 B2 | 1/2004 | Strickland et al. | |
| 6,766,800 B2 | 7/2004 | Chu et al. | |
| 6,848,443 B2 * | 2/2005 | Schmidt et al. | 128/200.23 |
| 2002/0046755 A1 | 4/2002 | DeVoss | |
| 2002/0124849 A1 | 9/2002 | Billette de Villemeur | |
| 2005/0028822 A1 | 2/2005 | Sleeper et al. | |
| 2005/0033247 A1 | 2/2005 | Thompson | |
| 2005/0051176 A1 | 3/2005 | Riggins | |
| 2005/0061326 A1 | 3/2005 | Payne, Jr. | |

FOREIGN PATENT DOCUMENTS

| | | |
|---|---|---|
| EP | 0 658 356 | 6/1995 |
| GB | 0532214 | 1/1941 |
| WO | WO 01/97892 A1 | 6/2000 |
| WO | WO 2005/079726 | 9/2005 |

* cited by examiner

NASAL VENTILATION INTERFACE AND SYSTEM

CROSS-REFERENCE TO RELATED APPLICATION

This application is a continuation in part of application Ser. No. 10/910,616, filed on Aug. 4, 2004 and claims benefit under 35 U.S.C. 120. Also, this application claims benefit under 25 U.S.C. 120 to application Ser. No. 10/830,034 filed Apr. 23, 2004, of which application Ser. No. 10/910,616 was a continuation in part. Additionally, this application claims the benefit to U.S. Provisional Patent Application No. 60/501,028, entitled "Ultimate Performance Cannula," filed Sep. 9, 2003, and U.S. Provisional Patent Application No. 60/492,282, entitled "Variable Exhaust Ports," filed Aug. 5, 2003, the disclosures of which are expressly incorporated by reference herein in their entirety.

BACKGROUND OF THE INVENTION

1. Field of the Invention

Exemplary embodiments of the invention are directed to a nasal ventilation interface adaptable to be connected to a source of ventilation.

2. Discussion of Related Art

Obstructive sleep apnea syndrome (commonly referred to as obstructive sleep apnea, sleep apnea syndrome, and/or sleep apnea) is a medical condition which includes repeated, prolonged episodes of cessation of breathing during sleep. During a period of wakefulness, the muscles of the upper part of the throat passage of an individual keep the passage open, thereby permitting an adequate amount of oxygen to flow into the lungs. During sleep, the throat passage tends to narrow due to the relaxation of the muscles. In those individuals having a relatively normally sized throat passage, the narrowed throat passage remains open enough to continue to permit the adequate amount of oxygen to flow into the lungs. However, in those individuals having a relatively smaller sized throat passage, the narrowed throat passage prohibits the adequate amount of oxygen from flowing into the lungs. Additionally, a nasal obstruction, such as a relatively large tongue, and/or certain shapes of the palate and/or the jaw of the individual further prohibit the adequate amount of oxygen from flowing into the lungs.

The individual having the above-discussed conditions can stop breathing for one or more prolonged periods of time (e.g., 10 seconds or more). The prolonged periods of time during which breathing is stopped, or apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and/or depression.

Other medical conditions can also prevent individuals, including adults and infants, from receiving the adequate amount of oxygen into the lungs. For example, an infant who is born prematurely can have lungs that are not developed to an extent necessary to receive the adequate amount of oxygen. Further, prior to, during, and/or subsequent to certain medical procedures and/or medical treatments, an individual can be unable to receive the adequate amount of oxygen.

Under these circumstances, it is known to use a ventilation interface to apply a positive pressure to the throat of the individual, thereby permitting the adequate amount of oxygen to flow into the lungs. In the known ventilation interface, oxygen and/or room air containing oxygen is delivered through the mouth and/or nose of the individual. Known types of positive pressure applied by the known ventilation interface include continuous positive airway pressure (CPAP) in which a positive pressure is maintained in the throat passage throughout a respiratory cycle, bi-level positive airway pressure (BiPAP) in which a relatively high positive pressure is maintained during inspiration and a relatively low positive pressure is maintained during expiration, and intermittent mechanical positive pressure ventilation (IPPV) in which a positive pressure is applied when apnea is sensed (i.e., the positive airway pressure is applied intermittently or non-continuously).

One conventional ventilation interface for the application of such positive pressures includes a face mask that covers the nose and/or mouth, as well as a pair of nasal pillows that are inserted into corresponding nares of the naris.

In the conventional art, pressure must be applied between the required harness and the head of the individual to maintain the required seal. As a result, the harness is generally uncomfortable to wear, particularly when sleeping. The applied pressure often results in undesirable irritation and sores caused by movement of the mask and harness during periods of both wakefulness and sleep. Further, the required seal is generally difficult to maintain when the mask and harness is moved. The mask also generally applies an undesirable pressure to the sinus area that is adjacent to the nose, causing the nasal sinus airways to narrow. This causes an increase in the velocity of flow through the upper anatomical airways and a decrease in the lateral pressure against the nasal mucosal walls. Additionally, the tubing may fold undesirably exacerbating the above problem. The above-discussed combination of increased flow velocity and decreased pressure results in the removal of moisture from the mucosal walls during inspiration and may cause an undesirable drying and a burning sensation within the nares. As a result, the individual may remove the mask to alleviate these discomforts, consequently discontinuing the beneficial application of the positive pressure. Additionally the decreased pressure and increased air flow velocity deteriorate the laminar flow between the air input and output portions of the conventional mask.

For these reasons, it is desirable to provide an improved nasal ventilation interface that overcomes one or more of the above-discussed disadvantages.

SUMMARY OF THE EXEMPLARY EMBODIMENTS OF THE INVENTION

A first exemplary embodiment of the present invention provides a nasal ventilation interface including a cannula connectable to a source of ventilation gas via at least two ventilation connectors including at least one reservoir flange in close proximity with at least one nasal insert. The nasal ventilation interface further includes a seal portion positioned on a distal end of the at least one nasal insert and a central reservoir with at least one exhaust flange and an exhaust port positioned at a midpoint between the at least two ventilation connectors.

In a second exemplary embodiment, a nasal ventilation interface includes a cannula connectable to a source of ventilation gas via at least two ventilation connectors forming a first inflow portion. A reservoir flange forms a second inflow portion with at least one nasal insert. The nasal insert forms a third inflow portion and a first outflow portion. A seal portion with a substantially oval cross section is positioned on a distal end of the nasal insert. A central reservoir forms a second outflow portion. At least one exhaust flange forms a third outflow portion. An exhaust port positioned at a midpoint between the at least two ventilation connectors forms a fourth outflow portion and a fifth outflow portion.

A third exemplary embodiment describes a ventilation interface system. The system may include feed tubes, a y-connector and headgear engageable with a headgear flange on a cannula. The ventilation connectors are connectable to a source of ventilation gas via the feed tubes and y-connector. The at least two ventilation connectors form a first inflow portion. A reservoir flange forms a second inflow portion. At least one nasal insert and seal portion form a third inflow portion and a first outflow portion. A central reservoir forms a second outflow portion. At least one exhaust flange forms a third outflow portion. An exhaust port positioned at a midpoint between the at least two ventilation connectors forms a fourth outflow portion and a fifth outflow portion.

BRIEF DESCRIPTION OF THE DRAWINGS

Reference will now be made to the exemplary embodiments of the invention, examples of which are illustrated in the accompanying drawings. Wherever possible, the same reference numbers will be used throughout the drawings to refer to the same or like parts

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

DETAILED DESCRIPTION OF THE EXEMPLARY EMBODIMENTS

The present invention provides a nasal ventilation interface system that may include a cannula that is configured to be connected to a ventilation source. The cannula may connect to a source of ventilation gas, such as oxygen and/or air containing oxygen. For example, the cannula may include a distal end that connects to a feed tube. The feed tube may then lead to a branch of a y-connector. The y-connector may then have an exterior surface and an interior surface that define a wall portion therebetween, and each of the exterior and interior surfaces may have a substantially circular or oval cross section. The y-connector may then have another branch that is connected with the source of the ventilation gas, such as a mechanical ventilator or some other source of gas. The source may apply a positive pressure through the cannula to the throat of the user, thereby permitting an adequate amount of oxygen or air to flow into the lungs. Although the figures show certain exemplary embodiments of the nasal ventilation system, it is to be understood that the ventilation system can be of any type. One or more exemplary embodiments of the present invention will now be described with reference to the drawings, wherein like reference numbers throughout the several views identify like and/or similar elements.

Figure 1:
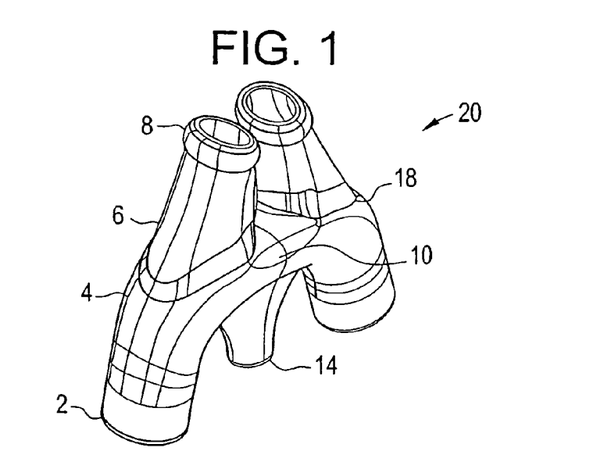
FIG. 1 shows a left front elevation view of an exemplary embodiment of a ventilation interface.

For example, as shown in FIG. 1, a cannula 20 may include a pair of ventilation connectors 2, at least one reservoir flange 4, at least one nasal insert 6, at least one seal portion 8, a central reservoir 10, an exhaust port 14, and at least one connection portion 18. These and other portions of the cannula 20 will now be further described.

Ventilation connectors 2 couple the cannula 20 to a ventilation source (not shown). Ventilation connectors 2 may be shaped and configured to connect to a wide variety of ventilation sources, such as a mechanical ventilator, pump, or tank. For example, ventilation connectors 2 may be configured to connect to a source of ventilation gas via one or more feed tubes and a y-connector (not shown). Other types of ventilation connectors may be used as part of the cannula 20.

Reservoir flange 4 provides a reservoir for air to flow from the ventilation connector 2 to other parts of the cannula 20. For example, reservoir flange 4 may be coupled to the nasal insert 6, the central reservoir 10, and the exhaust flange 12.

Nasal insert 6 provides a structure for extending the cannula 20 into a user's nares. Nasal insert 6 may comprise at its distal end a seal portion 8. The seal portion 8 may have a substantially oval cross section in order to assist with fitting nasal insert 6 inside a user's nasal passages. The seal portion 8 may also be configured to receive a skirt (not shown) to prevent leakage. Nasal insert 6 may also be coupled at its proximal end to the central reservoir 10.

The seal portion 8 and/or at least one nasal insert 6 may be made of an elastic material. The elastic material may be chosen such that its resiliency is sufficient to retain the cannula 20 in the nares of a user. Further, the seal portion 8 and/or the nasal insert 6 may expand in response to the positive pressure of the ventilation gas, thereby aiding in the retention of the cannula 8 within the nares. The seal portion 8 may be retained entirely in the user's nares by friction between the seal portion 8 and the user's nares. Alternatively, the nasal insert 6 and seal portion 8 may be made of less elastic material that deforms only slightly and instead the cannula 20 may be held in place by headgear (not shown) that is attached to the user.

Central reservoir 10 provides an additional volume of air or gas that, for example, allows for a decreased flow velocity through cannula 20 without a drop in pressure. In addition, central reservoir 10 may be shaped in a variety of ways to optimize the airflow through the cannula 20.

For example, the central reservoir 10 may be shaped to allow a laminar flow through the cannula 20 between the nasal insert 6 and the exhaust port 14. In particular, the central reservoir 10 may have a shape and volume that is sufficient to slow the velocity of air or gas without dropping its pressure. This feature may be considered useful in increasing the effectiveness of the cannula 20 for treating sleep apnea.

During sleep, the exhalation of a person is driven by the elasticity of the lungs. For patients that use conventional sleep apnea devices, the contraction of the lungs during exhalation can become static during sleep, which interrupts the adequate exhalation and release of carbon dioxide. This may happen frequently with patients prescribed with conventional sleep apnea devices that use pressures outside the normal range of 8 cm $H_2O$ to 12 cm $H_2O$ which may be from 3 cm $H_2O$ to 25 cm $H_2O$ or higher. These conventional devices sometimes have extreme variations in continuous positive airway pressures, greater than the elasticity of the lung.

In contrast, in accordance with some embodiments of the present invention, a ventilation interface system that uses the cannula 20 with the central reservoir 10 can provide the ventilation gas from the ventilation source to the nares at a lower velocity thereby decreasing a drop in pressure and with improved laminar flow because the central reservoir 10 can hold an increased volume of air or gas. The resulting decrease in flow velocity decreases lateral pressure and in turn decreases the amount of moisture removed from the mucosal walls of a user, which increases the comfort of the user. Accordingly, the ventilation interface system consistent with the principles of the present invention may provide better comfort and functionality and may be more economical to produce over the conventional systems.

Referring now back to FIG. 1, an exhaust port 14 may be provided with central reservoir 10. The exhaust port 14 provides an outlet of air or gas from central reservoir 10 and assists with optimizing the airflow through the cannula 20. For example, as shown in FIG. 1, the exhaust port 14 may be positioned on the central reservoir 10 midway between the ventilation connectors 2. The cannula 20 may include a single exhaust port 14 with a substantially circular cross section.

Alternatively, the exhaust port 14 may be configured with a mechanism, such as a dial or valve, which increases or decreases the size of the internal diameter of the exhaust port 14 and varies the exhaust flow. This would enable various settings to be fitted to the various embodiments of the present invention.

As one non-limiting example, a doctor could prescribe a particular aperture setting to accommodate a particular patient's needs, thereby reducing the tendency for incoming pressure to overpower the elasticity of the lungs and prevent exhalation. For example, the mechanism may be helpful for CPAP users or other patients prescribed with excessive pressures ranging from 3 cm $H_2O$ to 25 cm $H_2O$ or higher. For some patients, the ranges may be from 5 cm $H_2O$ to 20 cm $H_2O$, 8 cm $H_2O$ to 15 cm $H_2O$ or 10 cm $H_2O$ to 12 cm $H_2O$.

In addition to treating sleep apnea, the mechanism may be integrated or removable from the cannula 20 and configured to facilitate flow of any type of gas that may be used in a dental office or hospital. For example, the cannula 20 may be fitted with a mechanism to allow for the administration of general anesthesia or other type of gas, such as a local anesthetic gas.

Referring to FIGS. 8–14, a cannula 20 may include an exhaust port 14 configured with an adjustable dial 42 with an elongated handle 44. The elongated handle 44 may be positioned substantially perpendicular to the adjustable dial 42. The elongated handle 44 may be used to turn the adjustable dial 42 which alters an internal diameter of the dial. Turning the elongated handle 44 in a clockwise direction opens the internal diameter of the adjustable dial 42 and turning the elongated handle 44 in a counterclockwise direction closes the internal diameter of the adjustable dial 42. The adjustable dial 42 with an elongated handle 44 may be detachable from the cannula 20 and replaceable with another adjustable dial such as, a dial without a handle 46 or a dial with specific flow settings 50. Any dial 42, 46 or 50 may be configured to snap into an exhaust port 14 or be held in by friction. Alternatively, any of the above described dials 42, 46 or 50 may be integrated into a cannula device 20. The cannula may include multiple exhaust ports 14 requiring multiple dials 42, 46 or 50 to properly adjust the flow velocities achieving the beneficial effects described above.

Figure 11:
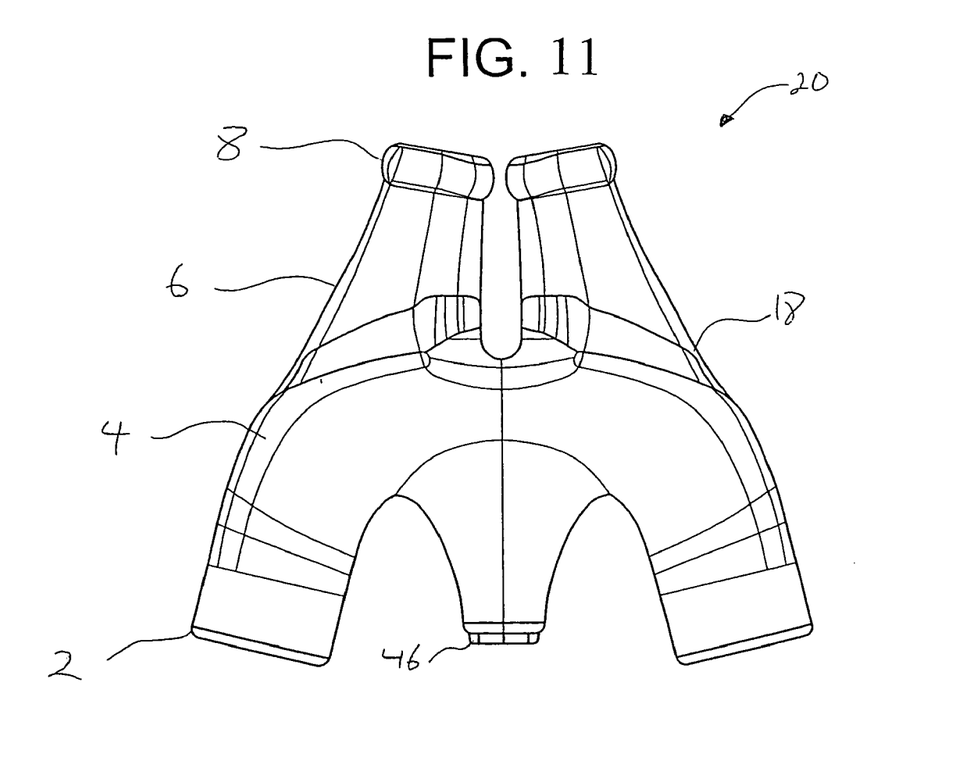
FIG. 11 shows a front side view of a fourth exemplary embodiment of a ventilation interface.
Figure 12:
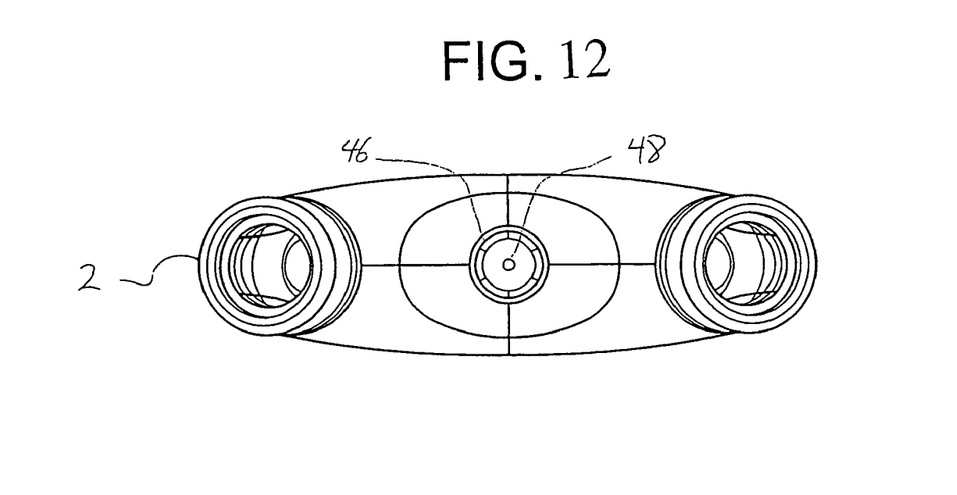
FIG. 12 shows a bottom view of a fourth exemplary embodiment of the ventilation insert of FIG. 11.

Likewise, referring to FIGS. 11–12, the internal diameter 48 of the dial without a handle 46 may be adjusted by turning the dial 46 in a clockwise direction to open the internal aperture 48 and counterclockwise direction to close the internal aperture 48.

Figure 13:
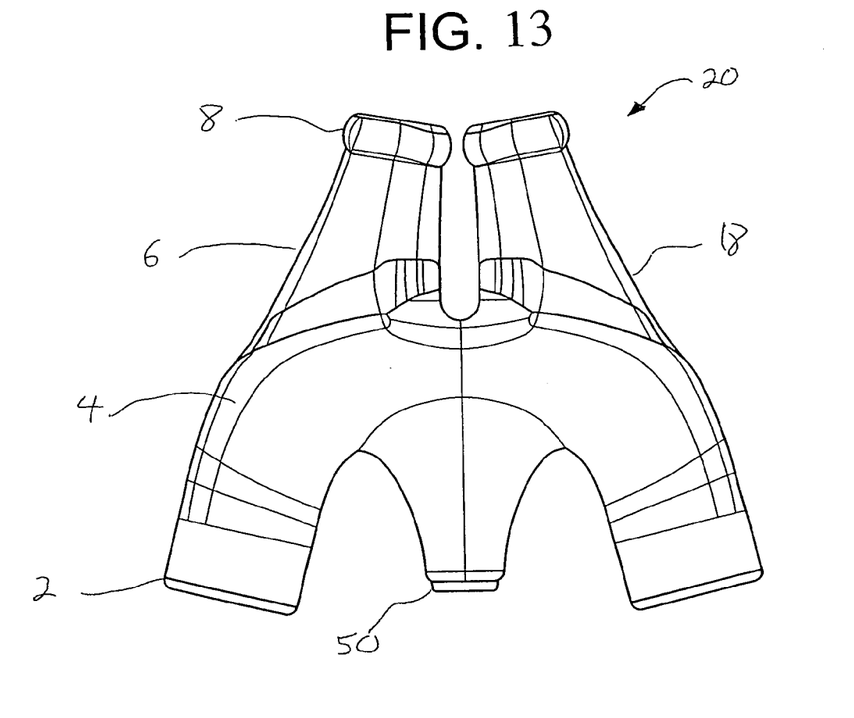
FIG. 13 shows a front side view of a fifth exemplary embodiment of a ventilation interface.
Figure 14:
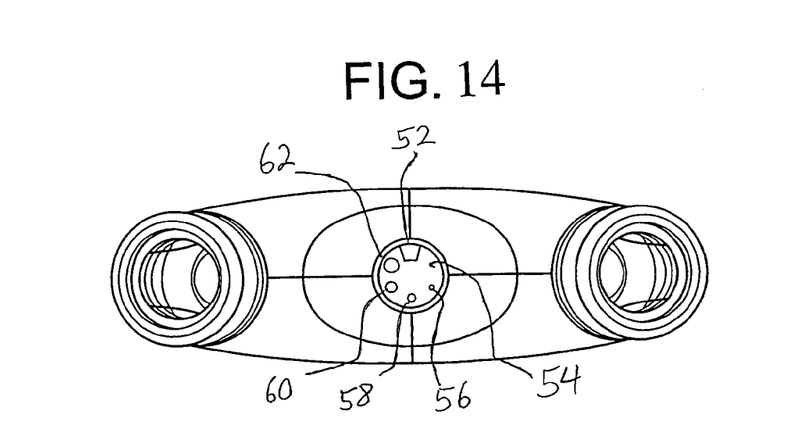
FIG. 14 shows a bottom view of a fifth exemplary embodiment of the ventilation insert of FIG. 13.

Similarly, referring to FIGS. 13–14 a dial with specific flow settings 50 may include a cut out 52. As the dial is turned in a counterclockwise direction the ultra low velocity opening 54, low velocity opening 56, the medium velocity opening 58, the medium plus velocity opening 60 and the high velocity opening 62 each respectively pass under the cut out 52 adjusting the specific flow setting. As one non-limiting example a physician, may prescribe a medium velocity flow setting 58 for a patient with an extreme pressure to achieve the beneficial effects described above.

Referring again back to FIG. 1, the cannula 20 may also include the connection portion 18, which provides a coupling structure for nasal insert 6. For example, connection portion 18 may be configured to allow for removable nasal inserts, such as nasal insert 6. Nasal insert 6 may, for example, be removable and replaceable for cleaning or may come in different sizes.

In addition, connection portion 18 may provide a structure for attaching other components to the cannula 20, such as a flange, connector, or loop for a strap or headgear.

Figure 2:
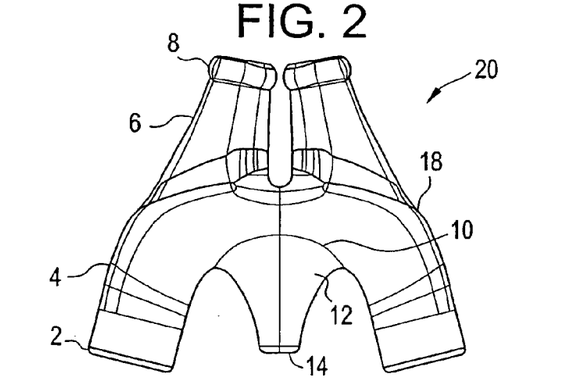
FIG. 2 shows a front side view of an exemplary embodiment of a ventilation interface.

Referring now to FIG. 2, a front side view is shown of an exemplary embodiment of the cannula 20. In addition to the components previously described with reference to FIG. 1, an exhaust flange 12 is now illustrated. As shown, the exhaust flange 12 extends from the central reservoir 10 and leads to the exhaust port 14. FIG. 2 also shows that the exhaust flange 12 and the exhaust port 14 may be positioned at a midpoint between the ventilation connectors 2. Of course other positions for the exhaust flange 12 and the exhaust port 14 may be used.

The exhaust flange 12 and exhaust port 14 may be configured to smooth the transition of air releasing out of the central reservoir 10. For example, as shown in FIG. 2, the exhaust flange 12 may have a decreasing circumference as it extends to exhaust port 14.

Figure 3:
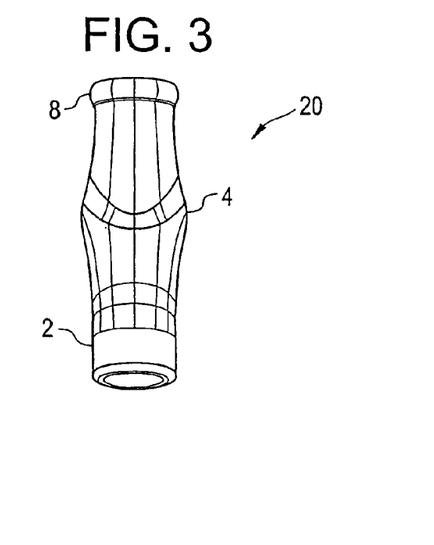
FIG. 3 shows a side view of an exemplary embodiment of a ventilation insert of FIG. 2.
Figure 4:
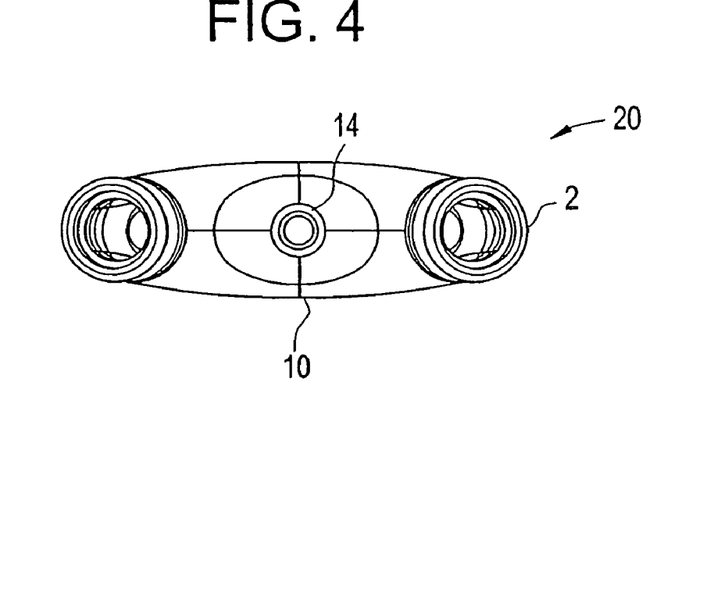
FIG. 4 shows a bottom view of an exemplary embodiment of the ventilation insert of FIG. 2.
Figure 5:
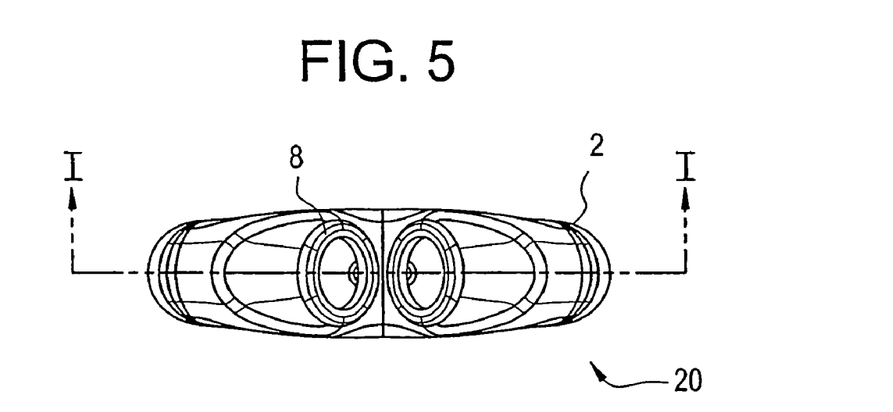
FIG. 5 shows a top view of the ventilation insert of FIG. 2.

Referring now to FIGS. 3, 4, and 5, different views are shown of an exemplary embodiment of the cannula 20. In particular, FIG. 3 shows a side view of the cannula 20 and illustrates the general shapes of connectors 2, reservoir flange 4, the nasal insert 6, and the seal portion 8. FIG. 4 shows a bottom view of the cannula 20 and illustrates the general shapes and locations of the connectors 2, the central reservoir 10, and the exhaust port 14. FIG. 5 shows a top view of the cannula 20 and illustrates the general shape and arrangement of the connectors 2, nasal insert 6, and the seal portion 8.

Figure 6:
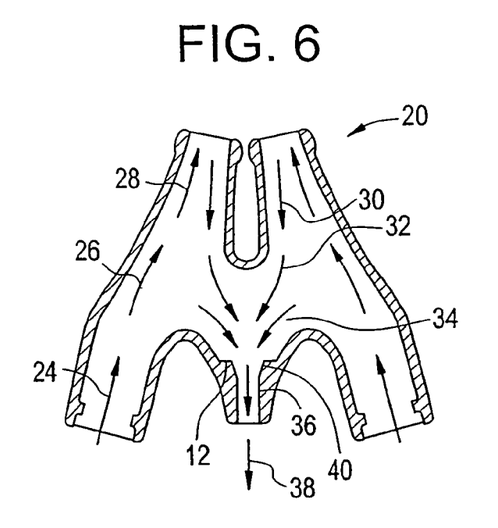
FIG. 6 shows a cross-sectional view taken from line I—I in FIG. 5.

FIG. 6 illustrates a cross-sectional view taken from line I—I in FIG. 5 and the general paths of flow through the cannula 20. For example, a first inflow portion 24 may begin in the cannula 20 from a ventilation source (not shown). The reservoir flange 4 forms a second inflow portion 26 which leads to nasal insert 6. Nasal insert 6 then forms a third inflow portion 28, which eventually leads into the nasal passages of the user.

During exhalation by the user, the nasal insert 6 forms a first outflow portion 30. The central reservoir 10 then forms a second outflow portion 32. As noted above, the central reservoir 10 may be shaped and configured such that the velocity of outflow portion 32 may be reduced without substantially affecting the pressure of the inflow portions or outflow portions. The exhaust flange 12 then forms a third outflow portion 34. The exhaust port 14 is configured and shaped to form a fourth outflow portion 36 and a fifth outflow portion 38. The fifth outflow portion 38 is then expelled out of exhaust port 14.

The exhaust port 14, the nasal insert 6, and the central reservoir 10 may be configured to allow for improved laminar flow by flow portions 24, 26, 28, 30, 32, and 34. In particular, the volume of the central reservoir 10 creates room for the gas and decreases the flow velocity of these flow portions and decreases the pressure drop. This decrease in flow velocity reduces any dryness and irritation that a user may otherwise have as a result of higher flow velocities which increase the venturi effect along the nasal mucosa membrane. The cannula 20 will increase the desired amount of pressure that prevents the apneas by increasing the number of air molecules. Additionally, the central reservoir 10 may allow for more laminar flow between the inflow portions 24, 26, and 28 and the outflow portions 30, 32, 34, and 36. The central reservoir 10 further reduce the likelihood of any tornadic activity between the second inflow portion 26 and second 32 and third 34 outflow portions.

Furthermore, the exhaust flange 12 and the exhaust port 14 may be shaped and configured to optimize a venturi or similar effect between the third 36 and fourth outflow 38 portions. In particular, the exhaust flange 12 at its top surface 40 may have a certain diameter that decreases as it extends to the exhaust port 14. This narrowing of the exhaust flange 12 and exhaust port 14 may cause a venture effect as outflow portion 36 is expelled into outflow portion 38. As described above, the exhaust port 14 may also include a mechanism, such as an adjustable dial or valve, that adjusts the aperture of the exhaust port 14.

Figure 7:
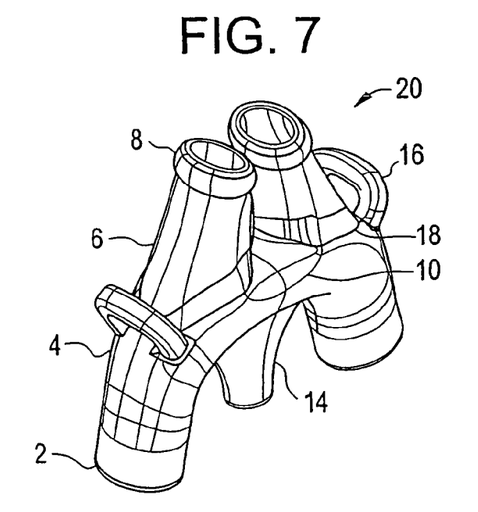
FIG. 7 shows an elevated front left view of a second exemplary embodiment of the nasal interface.
Figure 8:
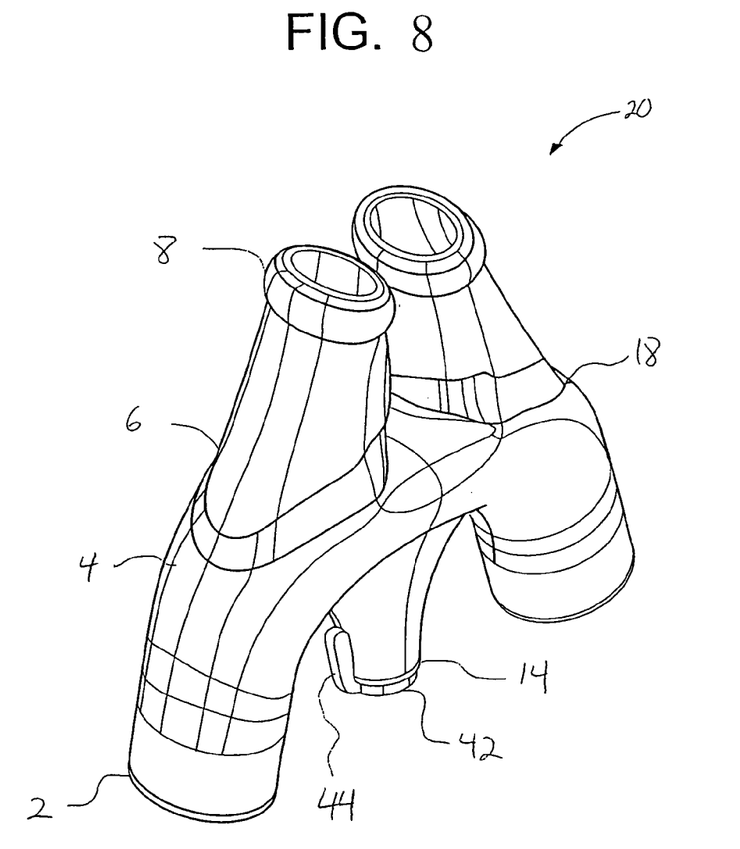
FIG. 8 shows a left front elevation view of a third exemplary embodiment of a ventilation interface.
Figure 9:
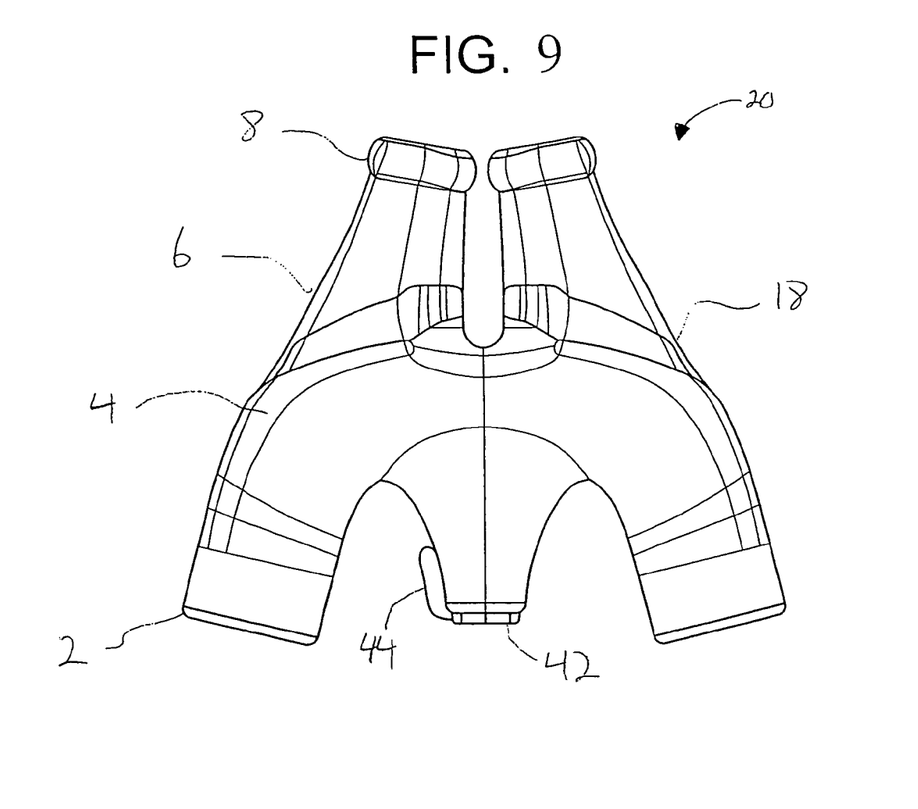
FIG. 9 shows a front side view of a third exemplary embodiment of a ventilation interface.
Figure 10:
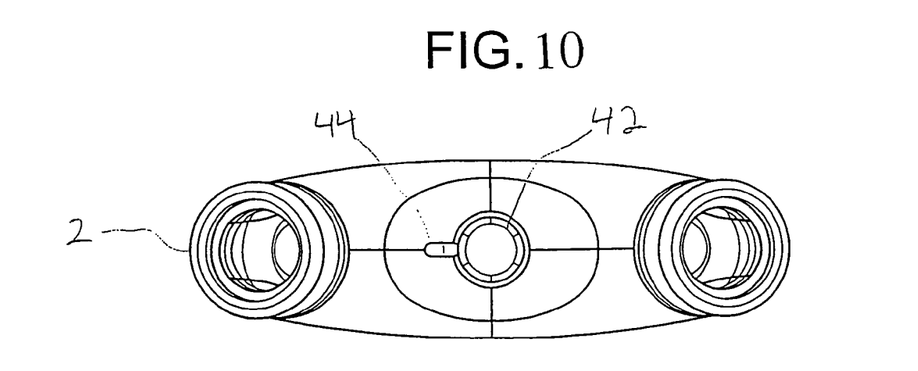
FIG. 10 shows a bottom view of a third exemplary embodiment of the ventilation insert of FIG. 9.

FIG. 7 shows an elevated front left view of another exemplary embodiment of the cannula 20. In particular, in addition to the components shown in FIGS. 1–5, the cannula 20 may also include at least one headgear flange 16. As previously described, the cannula 20 may be held in place by headgear (not shown), which is attached to the U-shaped headgear connector 16. The headgear flange 16 may be attached to an exterior portion of the cannula 20, such as at the connection portion 18. Headgear (not shown) may attach to the headgear flange 16 and/or connection portion 18 via Velcro®, snap, button, latch, loop or any other conventional connecting means.

Figure 15:
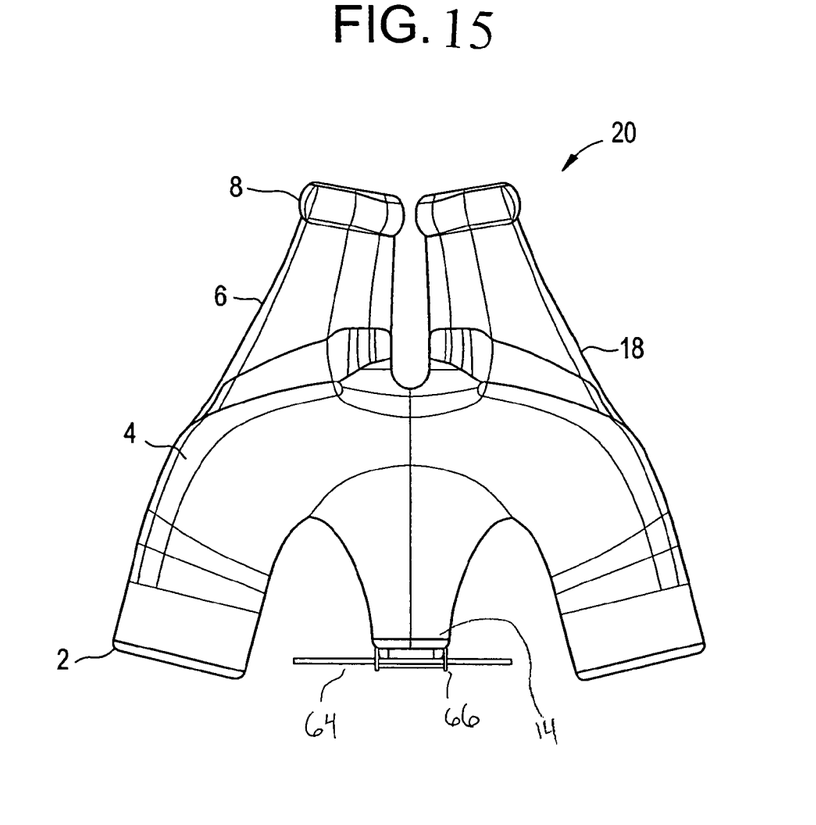
FIG. 15 shows a front side view of a sixth exemplary embodiment of a ventilation interface.

Referring to FIG. 15, a cannula 20 may include an exhaust port 14 configured with an adjustable slide 64 held onto exhaust port 14 using brackets 66. The adjustable slide 64 may be positioned substantially perpendicular to the exhaust port 14. The adjustable slide 64 may be moved to alter an internal diameter of the exhaust port. Moving the adjustable slide 64 to the left creates an exhaust port 14 diameter that is larger in diameter and moving the adjustable slide 64 to the right creates an exhaust port 14 that is smaller in diameter. The adjustable slide 64 may be detached from cannula 20 and replaced with another adjustable slide, such as a slide with different flow settings.

Figure 16:
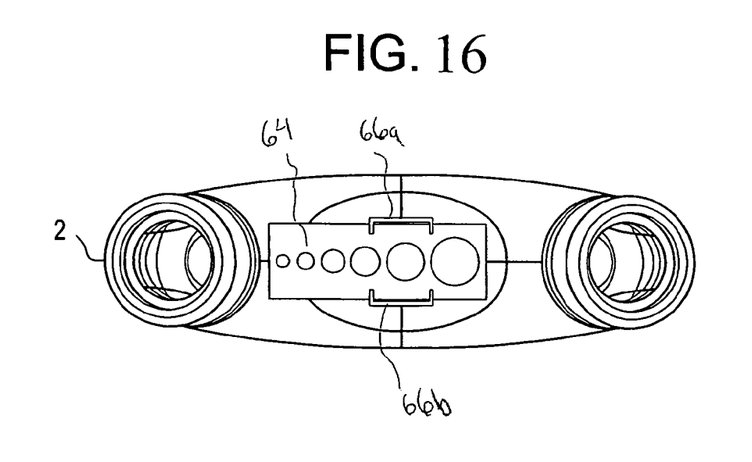
FIG. 16 shows a bottom view of a sixth exemplary embodiment of the ventilation interface shown in FIG. 15.

Referring now to FIG. 16, a rotated view of cannula 20 is shown. Slide 64 is shown with a variety of flow settings. Additionally, latches 66a and 66b hold the slide 64 against exhaust port 14 in such a manner as to allow a user to move slide 64 laterally as to change flow settings.

Figure 17:
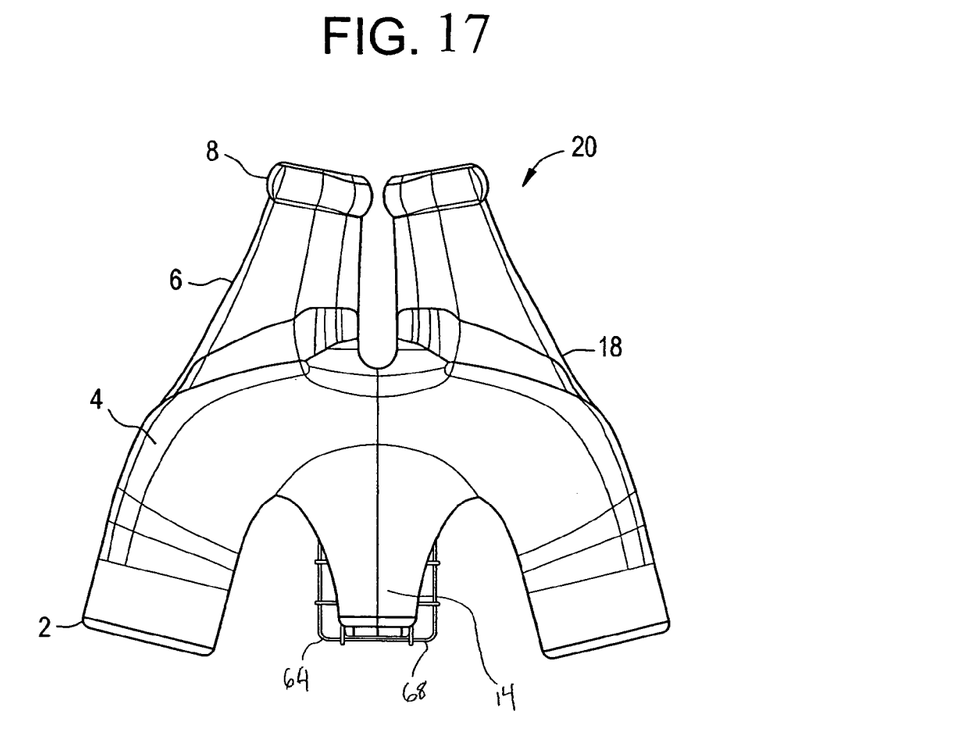
FIG. 17 shows a front side view of a seventh exemplary embodiment of a ventilation interface.

Referring to FIG. 17, a cannula 20 may include an exhaust port 14 configured with an adjustable slide 64 held against exhaust port 14 using brackets 68. The adjustable slide 64 may be positioned substantially along the three sides of the exhaust port 14. The adjustable slide 64 may be moved to alter an internal diameter of the exhaust port. Moving the adjustable slide 64 to the left creates an exhaust port 14 diameter that is larger in diameter and moving the adjustable slide 64 to the right creates an exhaust port 14 that is smaller in diameter. The adjustable slide 64 may be detached from cannula 20 and replaced with another adjustable slide, such as a slide with different flow settings.

Figure 18:
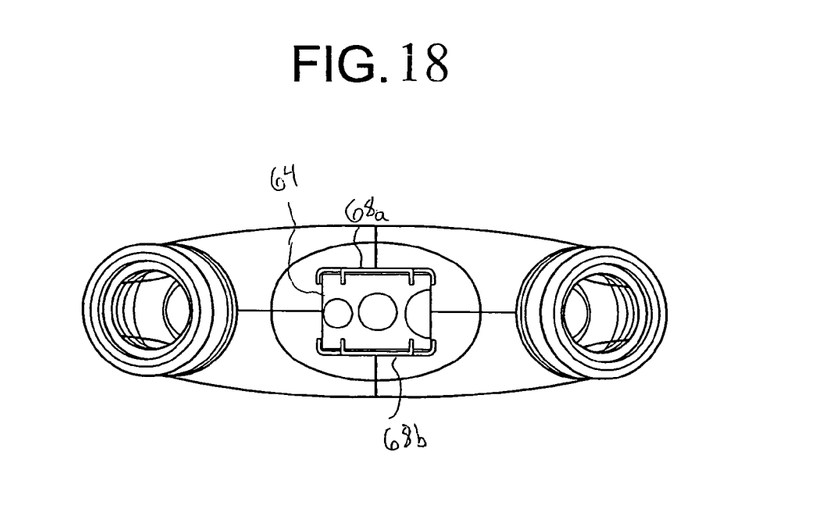
FIG. 18 shows a bottom view of a seventh exemplary embodiment of the ventilation interface shown in FIG. 17.

Referring now to FIG. 18, a rotated view of cannula 20 is shown. Slide 64 is shown with a variety of flow settings. Additionally, latches 68a and 68b hold the slide 64 against each side of exhaust port 14 in such a manner as to allow a user to move slide 64 laterally as to change flow settings.

Numerous additional modifications and variations of the exemplary embodiment of the present invention are possible in light of the above teachings. It is therefore to be understood that within the scope of the appended claims, exemplary embodiments of the present invention may be practiced otherwise than as specifically described herein.

What is claimed is:

1. An adjustable slide interface comprising:
   a substantially rectangular slide configured to be attachable to a nasal cannula with at least one flow velocity opening including a flow velocity cut out;
   wherein when the substantially rectangular slide is moved laterally at least one flow velocity opening passes over the flow velocity cut out.

2. The adjustable slide according to claim 1 wherein the substantially rectangular slide mechanism is configured to snap into an exhaust port.

3. The adjustable slide interface according to claim 1 wherein the substantially rectangular slide mechanism is configured be held in an exhaust port by brackets.

4. The adjustable slide interface according to claim 1 wherein the substantially rectangular slide is made from at least one of rubber, plastic, silicone, polyethylene or polyurethane.

* * * * *